(12) United States Patent
Tanaka

(10) Patent No.: US 11,207,450 B2
(45) Date of Patent: Dec. 28, 2021

(54) BREAST PUMP

(71) Applicant: PIGEON CORPORATION, Tokyo (JP)

(72) Inventor: Yuichiro Tanaka, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 756 days.

(21) Appl. No.: 15/775,179

(22) PCT Filed: Nov. 11, 2016

(86) PCT No.: PCT/JP2016/083557
§ 371 (c)(1),
(2) Date: May 10, 2018

(87) PCT Pub. No.: WO2017/082400
PCT Pub. Date: May 18, 2017

(65) Prior Publication Data
US 2018/0369463 A1  Dec. 27, 2018

(30) Foreign Application Priority Data
Nov. 13, 2015 (JP) .............................. JP2015-223397

(51) Int. Cl.
*A61M 1/06* (2006.01)
*F04B 49/12* (2006.01)
(Continued)

(52) U.S. Cl.
CPC .............. *A61M 1/06* (2013.01); *A61M 1/74* (2021.05); *A61M 1/82* (2021.05); *F04B 49/12* (2013.01);
(Continued)

(58) Field of Classification Search
CPC ............ A61M 1/06; A61M 2205/3337; A61M 1/0031; A61M 1/0072; A61M 1/74;
(Continued)

(56) References Cited

U.S. PATENT DOCUMENTS

| 6,547,756 B1 * | 4/2003 | Greter ..................... A61M 1/06 604/346 |
| 2003/0004459 A1 * | 1/2003 | McKendry .............. A61M 1/06 604/74 |

FOREIGN PATENT DOCUMENTS

| EP | 1163915 A2 | 12/2001 |
| JP | 2007-501673 A | 2/2007 |

(Continued)

OTHER PUBLICATIONS

The extended European Search Report for the corresponding EP application No. 16864361.7 dated Apr. 17, 2019.
International Search Report of PCT/JP2016/083557.

*Primary Examiner* — Brandy S Lee
(74) *Attorney, Agent, or Firm* — Muncy, Geissler, Olds & Lowe, P.C.

(57) ABSTRACT

A breast pump according to the present invention includes a variable pressure generating unit, the variable pressure generating unit including a power driving unit including a stepping motor that is capable of rotating both normally and in reverse, and a negative pressure forming unit that creates a negative pressure state periodically by causing an elastic body to deform in accordance with a cycle period formed by the power driving unit, wherein the negative pressure forming unit is coupled to the expressing unit, and the stepping motor is capable of modifying an amplitude of the cycle period and the cycle period during negative pressure formation as desired. Hence, a suction pressure and a pressure (Continued)

increase/decrease cycle can both be set as desired, and moreover, a breast pump that uses electric power can be constructed compactly.

11 Claims, 21 Drawing Sheets

(51) Int. Cl.
  *F04B 49/20* (2006.01)
  *A61M 1/00* (2006.01)
  *F16H 7/02* (2006.01)
  *F16H 19/06* (2006.01)
  *F16H 37/02* (2006.01)
  *F04B 45/027* (2006.01)

(52) U.S. Cl.
  CPC ............... *F04B 49/20* (2013.01); *F16H 7/02* (2013.01); *F16H 19/06* (2013.01); *F16H 37/02* (2013.01); *A61M 2205/3337* (2013.01); *F04B 45/027* (2013.01); *F16H 2019/0686* (2013.01)

(58) Field of Classification Search
  CPC ......... A61M 1/82; F04B 49/12; F04B 45/027; F04B 49/20; F16H 19/06; F16H 2019/0686; F16H 37/02; F16H 7/02
  See application file for complete search history.

(56) References Cited

FOREIGN PATENT DOCUMENTS

| | | |
|---|---|---|
| JP | 2013-102867 A | 5/2013 |
| JP | 2014-128685 A | 7/2014 |
| WO | 99/44650 A1 | 9/1999 |
| WO | 2015-055503 A1 | 4/2015 |

* cited by examiner

BREAST PUMP

TECHNICAL FIELD

The present invention relates to an improvement of a breast pump for expressing breast milk.

BACKGROUND ART

A breast pump used by a mother or the like to express breast milk includes, for example, a horn portion that contacts the breast, and negative pressure forming means such as a pump for creating negative pressure in a space formed when the horn portion contacts the breast. Breast milk suctioned into the negative pressure space drops into a bottle or the like so as to be collected therein, and a negative pressure forming unit and the pump are connected such that air can pass therebetween.

More specifically, in a proposed breast pump (see PTL 1), when generating an expressing action by forming negative pressure in the interior of a horn portion that is fitted tightly to the breast and expressing breast milk by suction, a suction pressure and a pressure increase/decrease cycle can both be set as desired to respond to the needs of the user.

CITATION LIST

Patent Literature

[PTL 1] Japanese Patent Application Publication No. 2013-102867

SUMMARY OF INVENTION

Technical Problem

With this type of breast pump, however, a large main body unit is required to obtain the power required for an expressing operation electrically, and a chamber having a large capacity is required to increase the negative pressure to the required amount. As a result, a corresponding increase occurs in the overall size of the device.

A device of this type may not cause a problem when installed in a permanently fixed manner in a hospital or the like, for example, but when the device is moved around the hospital or the user uses the device at home, the excessive size of the device may cause inconvenience.

The present invention has been designed to solve the problem described above, and an object thereof is to provide a breast pump in which it is possible to realize a mechanism unit that is compact but capable of obtaining sufficient power.

Solution to Problem

The present invention is a breast pump that includes: a variable pressure generating unit connected to an expressing unit that is brought into contact with a breast of a user, and alternately forming a negative pressure state below atmospheric pressure and a higher pressure than the pressure of the negative pressure state, the variable pressure generating unit including a power driving unit including a stepping motor that is capable of rotating both normally and in reverse, and a negative pressure forming unit that creates the negative pressure state by causing an elastic body to deform in accordance with a cycle period formed by the power driving unit, wherein the negative pressure forming unit is coupled to the expressing unit, and the stepping motor is capable of modifying an amplitude of the cycle period and the cycle period during negative pressure formation as desired.

According to the configuration described above, the stepping motor of the power driving unit is capable of modifying the amplitude of the cycle period and the cycle period itself as desired, thereby eliminating the need to provide a large component or member such as a buffer between a mechanism unit and an expression unit. As a result, the entire breast pump can be constructed compactly.

Further, since the power driving unit includes the stepping motor that is capable of rotating both normally and in reverse, a mechanism for implementing a negative pressure formation operation using the negative pressure forming unit can be formed easily, without using a large number of components.

Furthermore, since the power driving unit includes the stepping motor, desired rotation angles can be specified respectively during normal and reverse rotation operations of a motor shaft of the stepping motor, and a rotation speed thereof can also be determined as desired. Hence, the amplitude of the cycle period of negative pressure formation and a frequency (a cycle speed) of negative pressure formation can also be adjusted as desired. Moreover, a large amount of torque can be obtained even in a high-speed rotation region and a high-speed normal/reverse inversion region, and therefore an operation can be performed continuously without falling out-of-step.

Preferably, the breast pump further includes a mechanism unit installed with the power driving unit and an expression unit connected to the mechanism unit, wherein negative pressure formed by the mechanism unit is transmitted to the expression unit.

The mechanism unit for forming negative pressure is provided separately to the expression unit, and therefore the expression unit can be cleaned easily after each use.

Further, the expression unit can be determined for each user and exchanged for a dedicated expression unit used for each user, which is convenient.

Preferably, the power driving unit further includes a linear moving body that moves linearly in a rotation direction of a motor shaft of the stepping motor, and the linear moving body creates negative pressure by periodically increasing and reducing, in accordance with the cycle period, the size of a region of the negative pressure forming unit in which the negative pressure forming unit generates negative pressure, as the motor shaft repeatedly rotates normally and in reverse.

According to this configuration, the rotation shaft of the stepping motor rotates normally and in reverse, and it is therefore possible to convert the rotation of an ordinary motor into reciprocation and change the direction of the reciprocation basically using the linear moving body alone. Hence, the power driving unit can be constructed extremely compactly, and high energy conversion efficiency can be achieved.

Preferably, the power driving unit further includes a support shaft provided in parallel with the motor shaft, and an endless belt disposed between the motor shaft and the support shaft, wherein the power driving unit forms negative pressure transmitting a reciprocation operation of the endless belt to the negative pressure forming unit.

According to this configuration, by disposing the endless belt between the motor shaft and the support shaft, a power driving unit with a stable structure can be provided, and rotation from the stepping motor can be transmitted with stability to the negative pressure forming unit using a small number of components.

Preferably, the power driving unit further includes a reduction gear for reducing a rotation speed of the motor shaft, a support shaft provided in parallel with a shaft of the reduction gear, and an endless belt disposed between the shaft of the reduction gear and the support shaft, wherein the power driving unit forms negative pressure by transmitting a reciprocation operation of the endless belt to the negative pressure forming unit.

According to this configuration, the power driving unit includes the reduction gear, and therefore the power required for an expression operation can be obtained from a smaller output of the stepping motor. In other words, the reduction gear is capable of improving the torque of the stepping motor. Accordingly, the stepping motor can be reduced in size and weight. As a result, the power driving unit can be constructed extremely compactly.

Preferably, the reduction gear includes a first pulley fixed to the motor shaft, a second pulley having a larger diameter than a diameter of the first pulley, and a belt that couples the first pulley and the second pulley to each other, wherein a shaft of the second pulley serves as the shaft of the reduction gear.

According to this configuration, even when a distance between the stepping motor and the negative pressure forming unit is comparatively large, the reduction gear can reduce the rotation speed of the motor shaft of the stepping motor reliably by means of a simple structure.

Preferably, the reduction gear includes a first gear fixed to the motor shaft, and a gear train that meshes with the first gear in order to reduce a rotation speed of the first gear, and includes at least one gear, wherein a shaft of a final stage gear of the gear train serves as the shaft of the reduction gear.

According to this configuration, the reduction gear can be prevented from slipping when transmitting the output of the stepping motor to the linear moving body, and a larger output from the stepping motor can be transmitted to the linear moving body.

Preferably, the reduction gear includes a first sprocket fixed to the motor shaft, a second sprocket having a larger number of teeth than a number of teeth of the first sprocket, and a chain that couples the first sprocket and the second sprocket to each other, wherein a shaft of the second sprocket serves as the shaft of the reduction gear.

According to this configuration, even when the distance between the stepping motor and the negative pressure forming unit is comparatively large, the reduction gear can be prevented from slipping when transmitting the output of the stepping motor to the linear moving body, and a larger output from the stepping motor can be transmitted to the linear moving body.

Preferably, at least one linear moving body is fixed to the endless belt, and negative pressure is created by periodically increasing and reducing, in accordance with the cycle period, the size of the region of the negative pressure forming unit in which negative pressure is generated, the negative pressure forming unit being provided with the linear moving body.

According to this configuration, one or more negative pressure forming units can be provided simply by fixing at least one linear moving body to the endless belt, and as a result, one or more expression units can be driven by a single mechanism unit.

Preferably, the elastic body is a dome-shaped film-form member to which one end of the linear moving body is fixed, and the size of the region of the negative pressure forming unit in which negative pressure is generated is increased and reduced in accordance with displacement of the elastic body in a direction of a linear movement of the linear moving body.

According to this configuration, the elastic body provided as the film-form member is capable of forming the negative pressure state required for the expression operation by being displaced by a comparatively small amount. Further, the elastic body is displaced in the direction of the linear movement of the linear moving body, and can therefore be displaced so as to be unlikely to break, even when deformed repeatedly.

Preferably, the elastic body is a film-form member having a bellows structure capable of expansion and contraction, and the size of the region of the negative pressure forming unit in which negative pressure is generated is increased and reduced in accordance with expansion and contraction of the elastic body in a direction of a linear movement of the linear moving body. According to this configuration, the elastic body provided as a film-form member having a bellows structure capable of expansion and contraction can form the negative pressure state required for the expression operation by being deformed in an easily deformable state. As a result, the elastic body can be displaced such that a deformation load is suppressed, or in other words so as to be unlikely to break, even when deformed repeatedly.

Advantageous Effects of Invention

According to the present invention, as described above, the suction pressure and the pressure increase/decrease cycle can both be set as desired. Moreover, a breast pump that uses electric power can be constructed compactly.

DESCRIPTION OF EMBODIMENTS

Preferred embodiments of the present invention will be described in detail below with reference to the attached figures.

Note that the embodiments described below are preferred specific examples of the present invention, and therefore various preferred technical limitations are applied thereto. However, unless specific description indicating limitations on the present invention is provided below, the scope of the present invention is not limited to the following embodiments.

Figure 1:
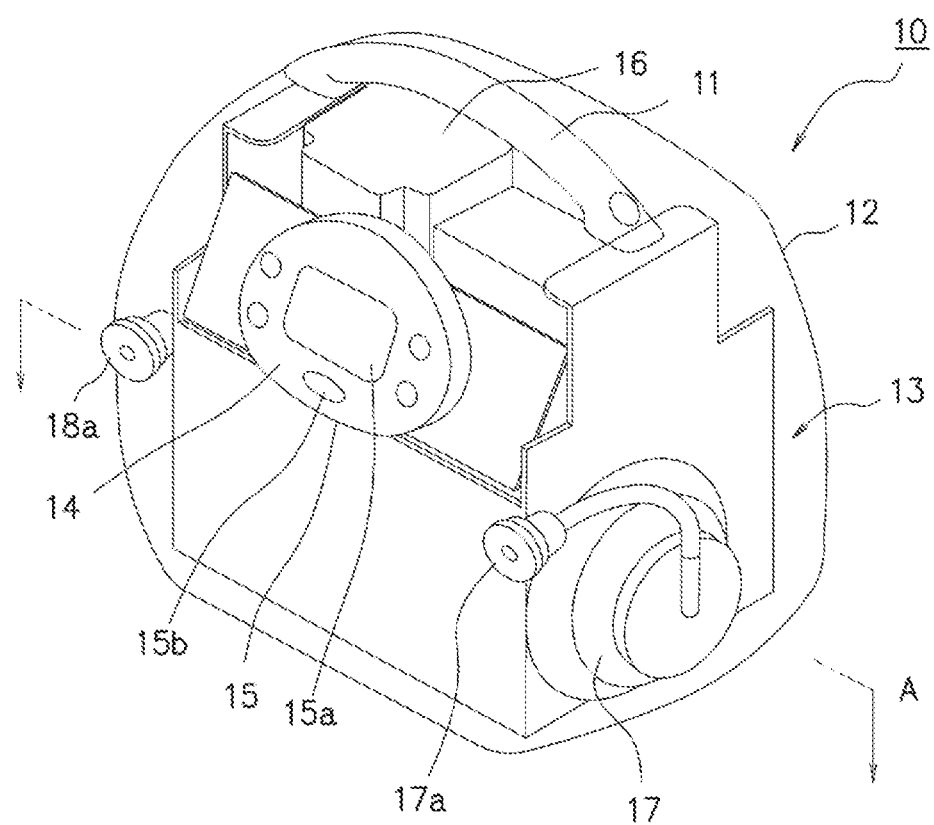
FIG. 1 is a schematic perspective view showing an internal structure of a mechanism unit for a breast pump according to an embodiment of the present invention.
Figure 2:
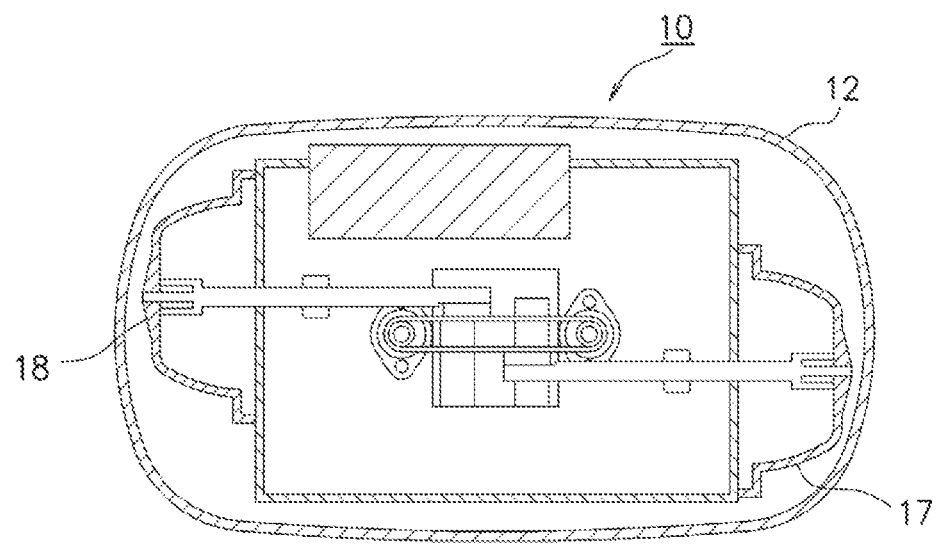
FIG. 2 is a schematic sectional view taken along an A-A line in FIG. 1.

FIG. 1 shows a mechanism unit 10 serving as a part of a breast pump according to an embodiment of the present invention, and FIG. 2 is a schematic sectional view taken along an A-A line in FIG. 1.

The mechanism unit 10 shown in FIG. 1 is obtained by housing mechanism units including a power driving unit in a housing 12, and for ease of understanding, in FIGS. 1 and 2, the housing 12, which is formed from synthetic resin or the like, has been made transparent so that main internal structures are visible.

The mechanism unit 10 does not house a buffer or the like for forming negative pressure, and therefore has a small overall size of approximately 0.005 cubic meters, for example.

A reference numeral 13 denotes a mechanical chassis provided inside the housing 12, and mechanism components and so on are incorporated into the mechanical chassis 13.

Negative pressure forming units 17, 18, to be described below, are provided on the outside of lower portions of left and right side walls of the mechanical chassis 13. Tubes extend respectively from the negative pressure forming units 17, 18, and as shown in FIG. 1, tip ends of the tubes are guided to a front surface of the housing 12 to form connection units 17a, 18a to and from which a tube of an expression unit, to be described below, is attached and detached.

A motor 16 included in the power driving unit is also housed in the housing 12. The motor 16 will be described in detail below.

A handle 11 is provided on an upper portion of the housing 12 so that the mechanism unit 10 can be carried easily.

A panel 15 is disposed on an upper portion of the front surface of the mechanism unit 10, and a display unit 15a formed from liquid crystal or the like is provided thereon. The display unit 15a displays required setting displays prior to an operation, operating states, other required displays, and so on. An operating button group 15b including a start switch is disposed on the periphery of the display unit 15a, and by means of the switch and the operating button group, a user can issue instructions in relation to an "Expression cycle", a "Suction pressure", and so on when operating the breast pump.

Figure 3:
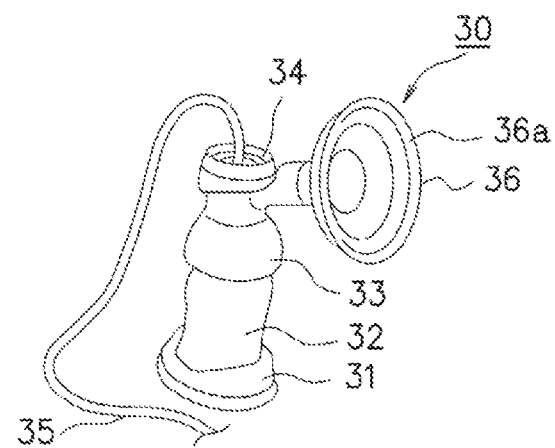
FIG. 3 is a schematic perspective view showing an example of an expression unit of the breast pump according to this embodiment of the present invention.
Figure 4:
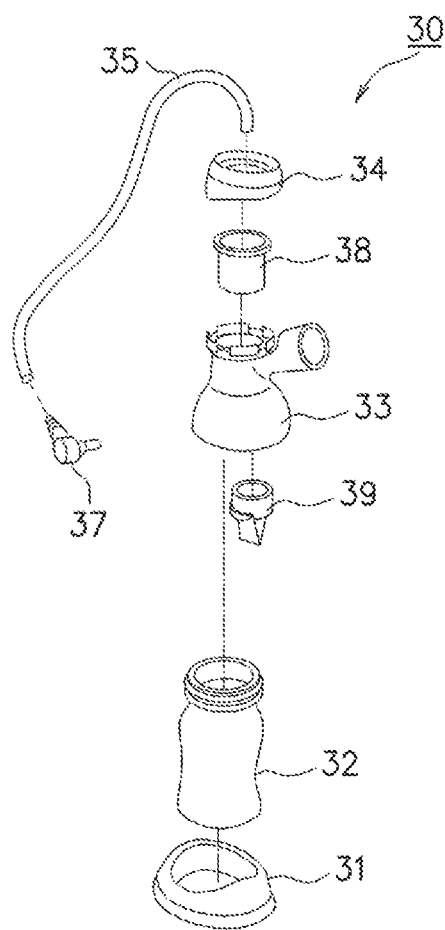
FIG. 4 is an exploded perspective view showing an example of the expression unit of the breast pump according to this embodiment of the present invention.

FIGS. 3 and 4 show an expression unit 30 connected to the mechanism unit. In this embodiment, one expression unit 30 can be connected to each of the connection units 17a, 18a illustrated in FIG. 1.

In FIGS. 3 and 4, the expression unit includes a bottle 32 that is supported on a support stand 31 and serves as a container for collecting expressed breast milk, and a hollow breast pump main body (also referred to hereafter as a "main body") 33 that can be attached to and detached from the bottle 32. The support stand 31 does not have to be used.

The entire main body 33 is formed from a strong, comparatively lightweight synthetic resin material, for example. The main body 33 is formed from polycarbonate, cyclic polyolefin, polyethersulfone, polyamide, polypropylene, or the like, for example.

A hollow, conical or horn-shaped expressing unit 36 that opens outward at a diagonal incline is provided integrally with an upper portion of the main body 33. During an expression operation, an airtight space is formed in the interior of the expressing unit 36 by fitting the expressing unit 36 tightly to a breast of the user.

In this embodiment, the expressing unit 36 is molded from a hard synthetic resin and preferably formed so that a separate, flexible expressing port deforming member 36a can be attached to and detached from the periphery of the horn-shaped opening on the tip end thereof. The expressing port deforming member 36a is formed from an elastic body made of silicone rubber, elastomer, natural rubber, or the like, for example.

As shown in FIG. 4, a cup 38 constituted by a tubular body that is elongated in a vertical direction and is open at one end and closed at the other end is housed in an internal space, not shown in the figures, of the main body 33 so as to communicate with the mechanism unit 10. The cup 38 divides the interior of the main body 33 into two spaces on a boundary between a primary side that serves as a passage for breast milk led from the expressing unit 36 side and a secondary side that communicates with a tube 35 that extends from the mechanism unit 10 and transmits negative pressure. In other words, the two spaces are sealed in airtight and watertight fashion so that gas leakage and liquid leakage are completely eliminated. The cup 38 is formed from a thin material through which air cannot pass, and is flexible enough to be easily deformed.

More specifically, the cup 38 is formed from an elastic body made of silicone, elastomer, natural rubber, or the like, for example, i.e. a material that is extremely flexible and will not break or the like even when deformed by repeated expansion and contraction.

A cap member 34 is attached detachably to an upper end of the main body 33 in order to block the space in which the cup 38 is housed. The tube 35 led from the mechanism unit 10 is connected to the cap member 34 so that the tube 35 communicates with the space on the aforementioned secondary side, which is defined as a space on the inner side of the cup 38.

Here, in a lower end of the main body 33, the space on the primary side, which serves as a passage for the breast milk led from the expressing unit 36 side, communicates with a small chamber valve 39 indicated by a reference numeral 39.

The small chamber valve 39 takes the overall shape of a cap formed from an elastic body made of silicone rubber, elastomer, natural rubber, or the like, and respective side walls thereof on a tip end side constitute inclined walls formed to gradually approach each other in a width direction toward a lower end. A slit is provided in the lower end where the respective side walls approach each other, and when a predetermined amount of expressed breast milk collects on the small chamber valve 39, the weight thereof, as well as pressure variation occurring when negative pressure is released, as will be described below, causes a valve body constituted by a duckbill valve to open, whereby the breast milk drops into the bottle 32. Further, by forming the slit in the lower end of the inclined walls, the small chamber valve 39 also functions as a check valve that prevents air in the bottle 32 from entering the small chamber when negative pressure is generated.

The expression unit 30 is configured as described above.

When negative pressure from the mechanism unit 10 side is applied to the cup 38, the cup 38 deforms within the airtight internal space, not shown in the figures, of the main body 33 in accordance with an air pressure difference with air on the outside of the cup 38 such that the internal space thereof is crushed, and as a result, a bottom portion thereof rises toward the cap member 34. More specifically, a volume of the cup 38 decreases greatly within the internal space of the main body 33, leading to a large reduction in air pressure in the space on the primary side, which communicates with the expressing unit 36, i.e. the space on the outside of the cup 38.

In other words, negative pressure increases in the space on the primary side, and therefore breast milk is suctioned from the breast, whereupon the expressed breast milk drops into the small chamber of the small chamber valve 39. When a fixed amount of breast milk collects in the small chamber, the valve body at the lower end of the small chamber valve 39 opens due to the weight of the breast milk, and as a result, the breast milk drops into the bottle 32.

When the negative pressure state is released in response to an operation of the mechanism unit 10, the cup 38 is displaced so as to return to its original form. Accordingly, the volume of the cup 38 in the main body 33 increases, leading to an increase in air pressure in the airtight space communicating with the expressing unit 36, i.e. the primary side space, and as a result, the breast milk suction pressure decreases.

By executing the operation described above repeatedly, the operation of the mechanism unit 10 functioning as a pressure modification unit is transmitted to the airtight space in the expressing unit by the movement of the cup 38, causing the negative pressure in the airtight space to increase and decrease, and as a result, a state close to a suckling action of an infant can be realized, whereby the breast milk expressed into the bottle 32 can be collected.

Next, the main mechanisms housed in the mechanism unit 10, including the pressure modification unit to be described below, will be described.

Figure 5:
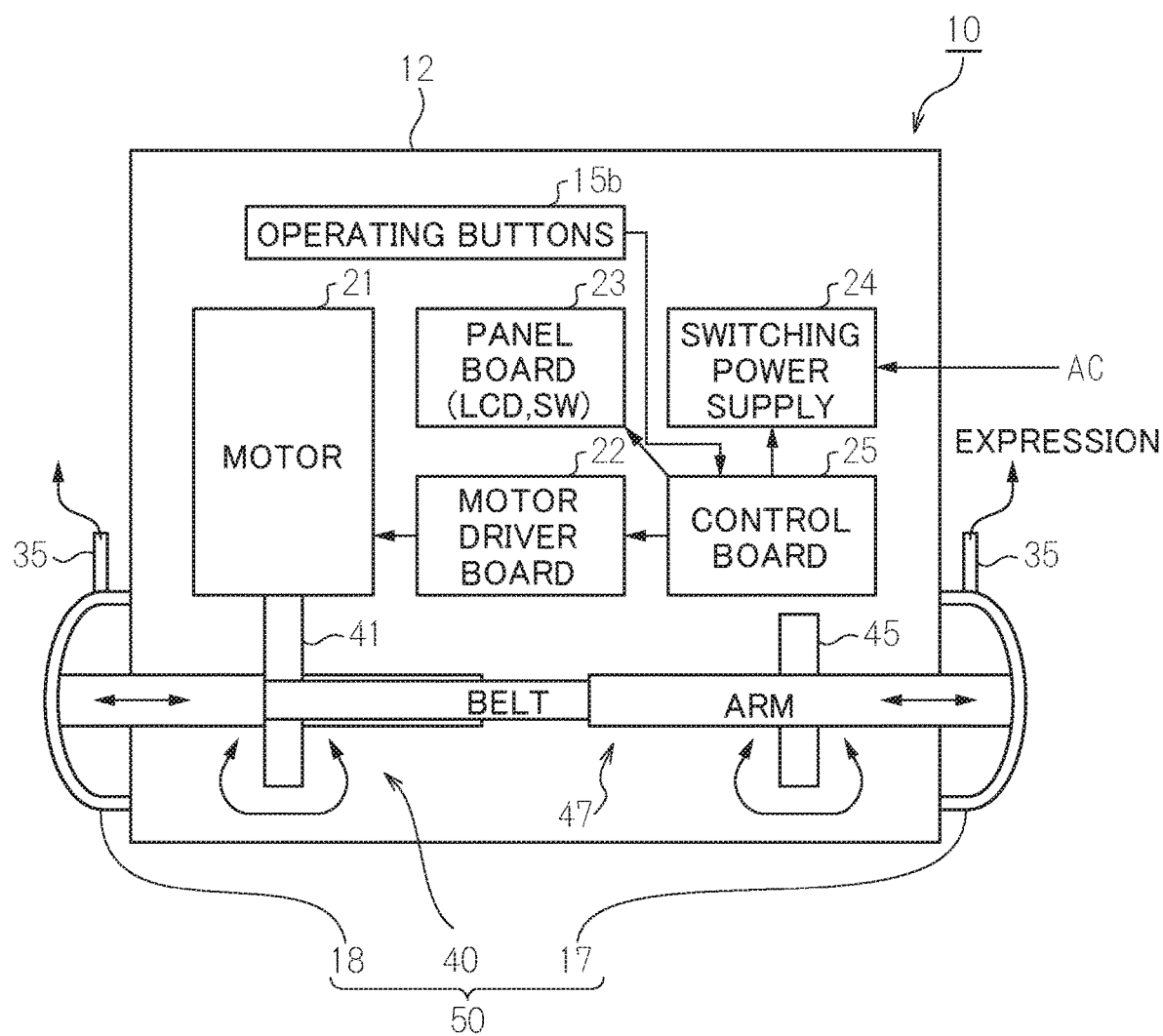
FIG. 5 is a block diagram showing an example of the mechanism unit of the breast pump according to this embodiment of the present invention.

FIG. 5 is a block diagram showing an electrical configuration housed in the mechanism unit 10 and the main mechanisms driven thereby.

In the figure, the mechanism unit 10 includes a switching power supply 24 into which a commercial power supply is input, a control board 25, a motor driver board 22, and a panel board 23.

The switching power supply 24 is capable of rectifying an input alternating current into a direct current and then converting the direct current into a required voltage. Power adjustment parts thereof include required circuits such as a starting circuit, a smoothing circuit, an overcurrent/overvoltage protection circuit, and a noise filtering circuit.

Note that a secondary battery, not shown in the figures, may be housed in the mechanism unit 10 so that two types of power supply, namely a commercial power supply and a battery, can be used.

As will be described below, a motor configured to be capable of modifying a cycle period during negative pressure formation and an amplitude of the cycle period as desired is used as the motor 21 employed as the power driving unit installed in the mechanism unit 10. A motor having a switchable rotation direction so as to be capable of rotating normally and in reverse is preferably used as the motor 21. A stepping motor, for example, can be used most preferably to realize these characteristics.

A drive current (a direct current) from the switching power supply 24 is applied to the motor driver board 22 via the control board 25. The motor driver board includes a pulse generator, and generates a pulse for driving the motor 21 formed from a stepping motor. Hence, the motor 21 is driven by a DC power supply. At this time, the scope of "driven by a DC power supply" includes not only a case in which the motor 21 is driven by supplying a DC power supply to the mechanism unit 10, but also a case in which the motor 21 is driven by converting an AC power supply supplied to the mechanism unit 10 into a DC power supply and then supplying the DC power supply obtained by conversion to the motor 21.

The control board 25 includes a CPU serving as a calculation unit, a RAM (a write/read memory) used as a predetermined work area, a ROM (a read only memory) for storing operating software and the like prepared in advance, and so on, and executes an overall operation of the breast pump.

The mechanism unit 10 further includes a variable pressure generating unit 50 for alternately forming a negative pressure state below atmospheric pressure and a higher pressure than the pressure of the negative pressure state. The variable pressure generating unit 50 includes a power driving unit 40 including the motor 21, and the negative pressure forming units 17, 18 that create the negative pressure state by causing an elastic body to deform. The power driving unit 40 uses the negative pressure forming units 17, 18 to form the negative pressure required to express breast milk.

Example configurations of the power driving unit 40 and the negative pressure forming units 17, 18 will be described in detail below.

Figure 6:
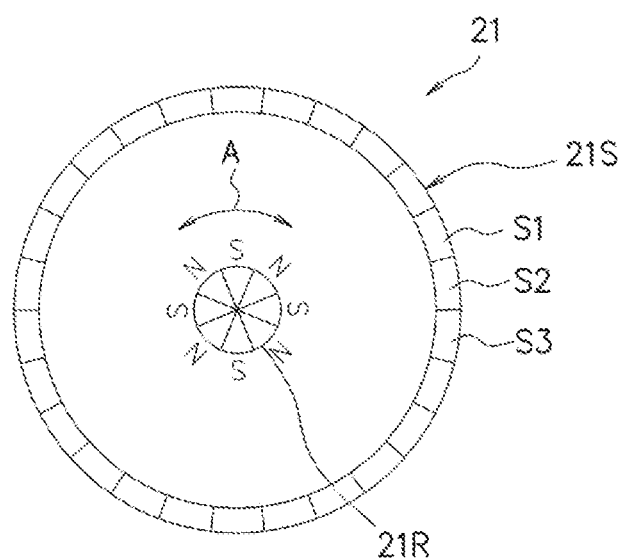
FIG. 6 is a pattern diagram showing a stepping motor serving as a part of a power driving unit of the breast pump according to this embodiment of the present invention.

FIG. 6 is a pattern diagram showing an example configuration of the motor 21.

The stepping motor shown in the figure includes a rotor 21R and a stator 21S wound in an annular shape around the rotor 21R. The rotor 21R is formed by arranging multi-pole magnetized permanent magnets in a circumferential direction so that S poles and N poles are disposed alternately. The stator 21S disposed in an annular shape on the outer side of the rotor 21R is an electromagnet, and as shown in the figure, is divided at equal angular intervals in the circumferential direction into small, continuous fan-shaped sectors S1, S2, S3, . . . . . .

Thus, during driving, when drive pulses are applied in sequence to coils disposed separately in the outside stator 21S at equal angular intervals of S1, S2, S3, . . . , and identical poles are aligned with circumferential direction magnetic poles of the opposing rotor 21R in the interior of the motor, a repulsion action is generated by repulsive force, and as a result, the motor 21 rotates.

As a result, a rotary shaft of the motor 21 (which is identical to a motor shaft) is rotated in such a manner that the shaft can be driven and stopped at each of the divided angle units in turn.

In other words, a drive angle (a step angle) per pulse is determined accurately from 360 degrees/the number of divisions of the stator S.

Hence, the motor 21 can be started and stopped, and driven to rotate intermittently both normally and in reverse, as shown by an arrow A, without the need for a measurement device such as an encoder.

A case in which a PM (permanent magnet) type stepping motor is used was described above, but any type of stepping motor, such as a variable reluctance (VR) type or a hybrid (HB) type, may be used.

When a stepping motor is used, a motor shaft 41 of the motor 21 can be driven to rotate and then stopped accurately in accordance with the number of drive pulses applied thereto.

Further, when the motor shaft 41 is to be driven in reverse, the motor shaft 41 can be rotated in reverse by inverting the drive pulse pattern.

Furthermore, by incorporating a mechanism unit to be described below into the motor 21 and determining the number of drive pulses, the amplitude of an expression timing cycle can be adjusted and determined, and moreover, a cycle frequency can be determined from a pulse width. Further, by adjusting the voltage generated by the switching power supply 24, torque adjustment can be implemented, thereby ensuring that a torque deficiency does not occur in a high rotation region.

Figure 7:
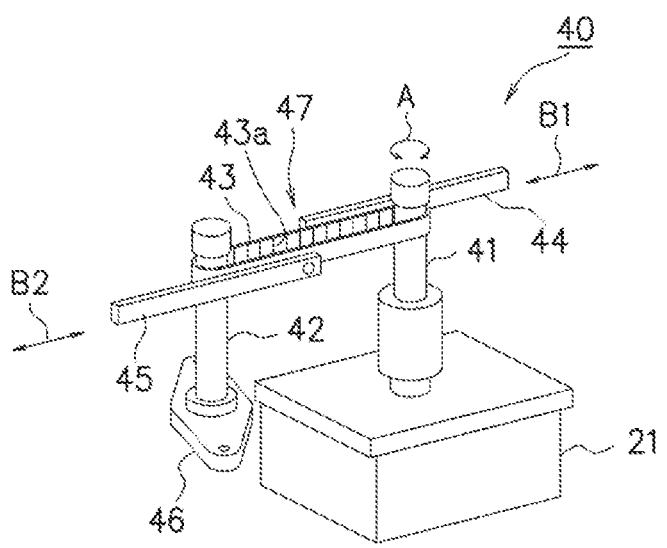
FIG. 7 is a schematic perspective view showing a mechanical configuration of the power driving unit of the breast pump according to this embodiment of the present invention.
Figure 8:
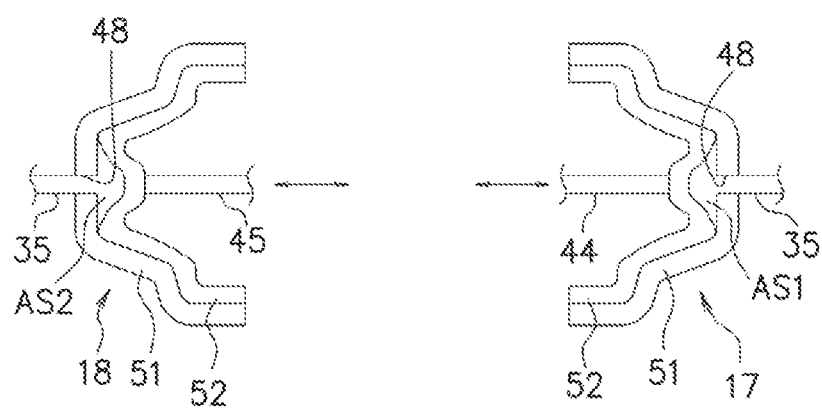
FIG. 8 is an illustrative view showing an example of main parts of a negative pressure forming unit of the breast pump according to this embodiment of the present invention.
Figure 9:
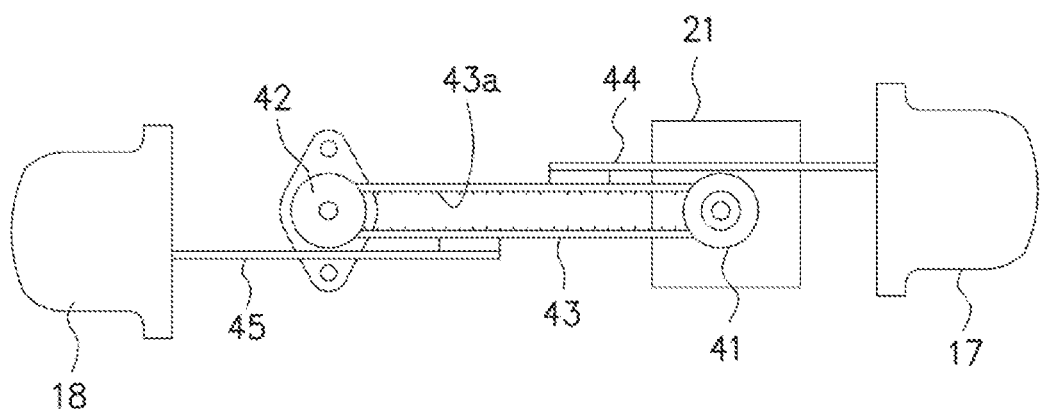
FIG. 9 is a schematic plan view of FIG. 7.

Referring to FIGS. 7, 8, and 9, the power driving unit 40 includes the motor 21 and a mechanism unit 47 that is incorporated into the motor 21. The motor 21 is a stepping motor, as described above, and specifically, the motor shaft thereof is capable of rotating both normally and in reverse, as indicated by an arrow A. Hence, in contrast to an ordinary motor, a gear box, a cam mechanism, or the like is not required to rotate the motor in reverse, and therefore the power driving unit can be constructed compactly. Another advantage of a stepping motor is that a stepping motor generates less noise than an ordinary motor.

As shown in FIGS. 8 and 9, the power driving unit 40 includes the motor shaft 41, which extends from one end of the motor 21, and a support shaft 42 disposed parallel to the motor shaft 41.

The support shaft 42 stands upright from a base 46, and the motor shaft 41 and the support shaft 42 are disposed in parallel in the interior of the housing 10 shown in FIG. 1 by fixing the base 46 to a bottom plate or the like of the housing 10 and erecting the support shaft 42 vertically on the base 46 so as to be free to rotate.

An annular endless belt 43 is suspended between the motor shaft 41 and the support shaft 42, and the motor shaft 41 and the support shaft 42 are joined to each other so that the support shaft 42 rotates in synchronization with the rotation of the motor shaft 41. Here, the endless belt 43 is preferably formed in the shape shown in the figure from a flexible but durable material. For example, a synthetic resin belt capable of slight expansion and contraction, a thin metal plate formed in a belt shape, or the like may be used. In this embodiment, specifically, chloroprene rubber is used.

The endless belt 43 does not require "elasticity", but in consideration of workability when suspending the endless belt 43 between the motor shaft 41 and the support shaft 42, the endless belt 43 may possess sufficient elasticity in a contraction direction to ensure that the belt does not become detached from the motor shaft 41 and the support shaft 42. When a contraction force of the endless belt 43 is too strong, however, the rotation force of the motor shaft 41 is impaired, which is undesirable.

Further, means for improving frictional force between the endless belt 43 and the motor shaft 41 and support shaft 42 may be disposed on a surface 43 of the endless belt 43 that contacts the motor shaft 41 and the support shaft 42. In other words, a non-slip portion is preferably applied to the contact surface 43a. The non-slip portion may be realized by means such as forming a large number of short projections at equal intervals in a lateral direction, for example, as shown in the figure, or improving the frictional force by roughening the contact surface 43a.

Two linear moving bodies can be fixed to the surface of the endless belt 43 at a predetermined distance from each other such that tip ends thereof face opposite directions.

In this embodiment, the linear moving bodies are thin, elongated, hard, rectangular rods 44, 45. Respective base end locations of the rods 44, 45 are fixed to the surface of the endless belt 43 by screws or the like, and the other ends face horizontally outward toward the left and right in FIG. 7.

Thus, when the motor shaft 41 rotates in the direction of the arrow A, the rods 44, 45 respectively reciprocate horizontally along arrows B1, B2.

Referring to FIG. 8, FIG. 8 shows relationships between the rods 44, 45 and the negative pressure forming units 17, 18.

The negative pressure forming units 17, 18 are exposed from respective side faces of the mechanical chassis 13 shown in FIG. 1, for example, and respectively include outside members 51 disposed on the outside of the mechanical chassis 13.

The outside members 51 are non-deforming parts formed from hard synthetic resin or the like, and are formed in a hollow dome shape so as to have an internal space.

Through holes 48 are formed in respective centers of the outside members 51.

Deforming members (elastic bodies) 52 are provided inside the respective outside members 51.

The deforming members 52 are durable film-form members such as membranes or diaphragms that are easily elastically deformed and do not break even when deformed repeatedly.

As shown in FIG. 8, the rods 44, 45 are respectively fixed at one end to the inner sides of the deforming members 52 so that when the rods 44, 45 move toward the inner side, the deforming members 52 are pulled inward, with the result that negative pressure forming spaces (regions in which negative pressure is generated) indicated by reference symbols AS1 and AS2 are created in the negative pressure forming units 17, 18. In other words, when the deforming members 52 deform in accordance with the cycle period formed by the power driving unit 40, the negative pressure forming units 17, 18 create a negative pressure state. More specifically, the negative pressure spaces AS1, AS2 are increased and reduced in size in response to displacement of the deforming members 52 in the direction of the linear movement of the rods 44, 45. To put it another way, the rods 44, 45 create negative pressure by increasing and reducing the size of the negative pressure spaces AS1, AS2 in accordance with the cycle period.

The negative pressure spaces AS1, AS2 are connected to the tubes 35 so that the formed negative pressure is transmitted through the tubes 35 to the expression unit 30 illustrated in FIGS. 3 and 4. In other words, the variable pressure generating unit 50 is connected to the expressing unit 36 through the tubes 35.

Hence, in the power driving unit 40, by disposing the endless belt 43 on the motor shaft 41 and the support shaft 42, a power driving unit with a stable structure can be provided, and the rotation of the motor 21 can be transmitted with stability to the negative pressure forming units 17, 18 using a small number of components. Further, the deforming members 52 provided as film-form members can form the negative pressure state required for the expression operation by being displaced by a comparatively small amount. Furthermore, the deforming members 52 are displaced in the direction of the linear movement of the rods 44, 45, and can therefore be displaced so as to be unlikely to break, even when deformed repeatedly.

Figure 10:
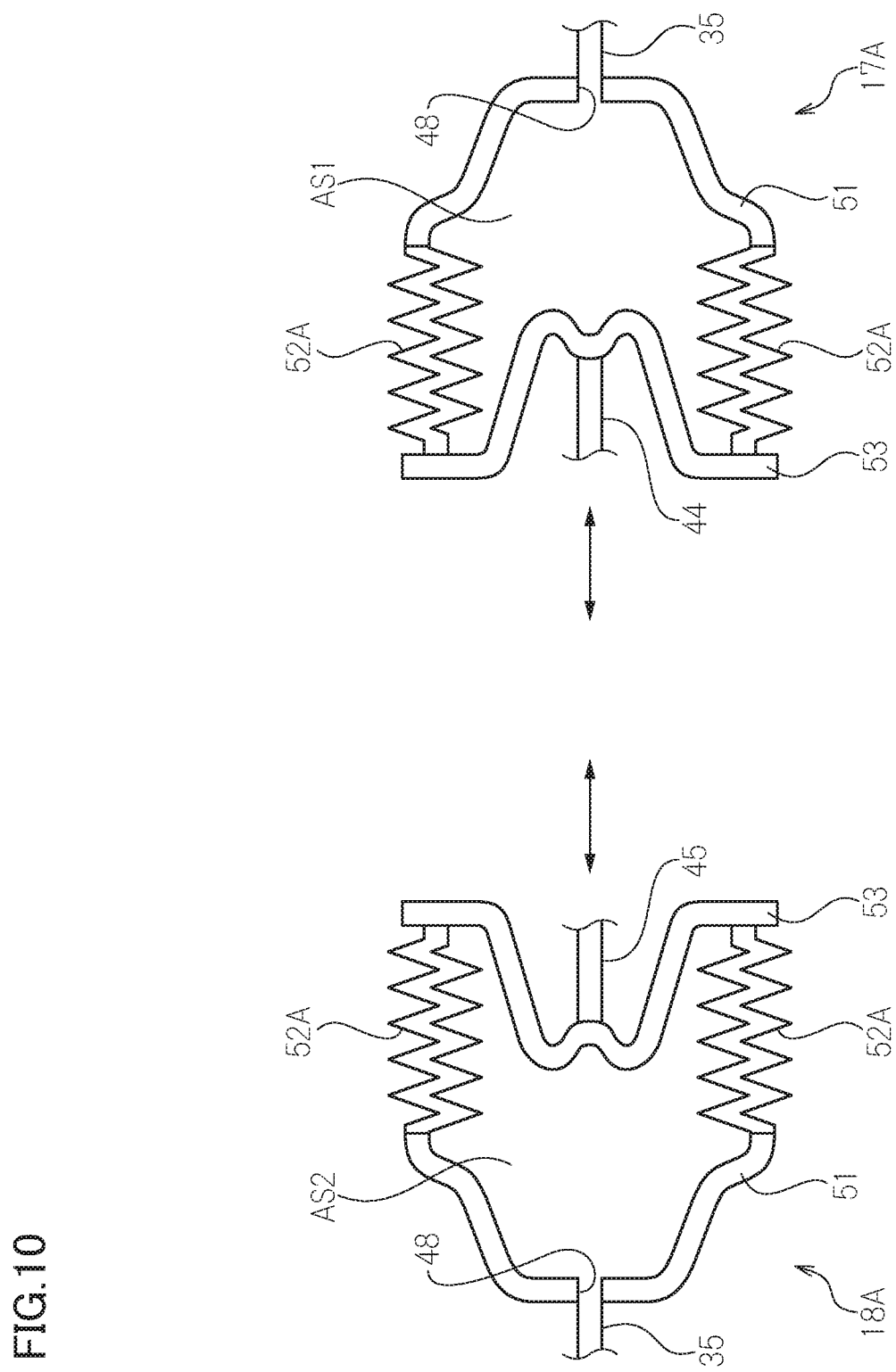
FIG. 10 is an illustrative view showing an example of main parts of a first modified example of the negative pressure forming unit.

FIG. 10 shows a first modified example of the negative pressure forming units.

In this modified example, negative pressure forming units 17A, 18A respectively include the outside members 51, deforming members (elastic bodies) 52A, and the inside members 53. The deforming members 52A are durable film-form members made of rubber or the like and having a bellows structure capable of expansion and contraction so as to be easily elastically deformed and so as not to break, even when deformed repeatedly. The deforming members 52A are provided between the outside members 51 and the inside members 53. More specifically, respective inside ends of the deforming members 52A are connected to the inside members 53 in an airtight state. Further, outside ends of the deforming members 52A are connected to the outside members 51 in an airtight state.

The inside members 53 are connected to the respective inside ends of the deforming members 52A, while respective central parts thereof are bent toward the outside members 51. The inside members 53 are non-deforming parts formed from hard synthetic resin or the like.

The rods 44, 45 are respectively fixed at one end to the inner sides of the inside members 53. When the rods 44, 45 move toward the inner side, the deforming members 52A and the inside members 53 are pulled inward, with the result that negative pressure forming spaces (regions in which negative pressure is generated) indicated by reference symbols AS1 and AS2 are created in the negative pressure forming units 17A, 18A (parts respectively surrounded by the outside members 51, the inside members 53, and the deforming members 52A).

In other words, when the deforming members 52A deform (more specifically, expand and contract) in accordance with the cycle period formed by the power driving unit 40, the negative pressure forming units 17A, 18A create a negative pressure state. More specifically, when the deforming members 52A expand and contract in the direction of the linear movement of the rods 44, 45, the negative pressure spaces AS1, AS2 are increased and reduced in size. To put it another way, the rods 44, 45 create negative pressure by increasing and reducing the size of the negative pressure spaces AS1, AS2 periodically in accordance with the cycle period. All other structures are similar to those of the negative pressure forming units 17, 18 described above in relation to FIG. 8.

According to this modified example, the deforming members 52A provided as film-form members having a bellows structure capable of expansion and contraction can form the negative pressure state required for the expression operation by deforming in an easily deformable state. As a result, the deforming members 52A can be displaced such that a deformation load is suppressed, or in other words so as to be unlikely to break, even when deformed repeatedly.

Figure 11:
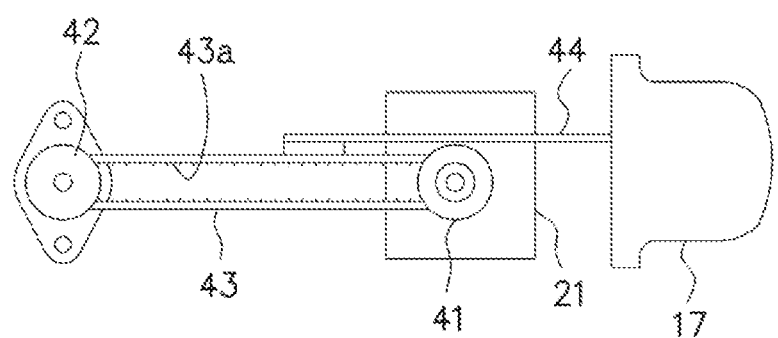
FIG. 11 is a view illustrating a modified example of the configuration shown in FIG. 9.

FIG. 11 shows an example configuration in which only one rod 44 is fixed to the endless belt 43 such that only one negative pressure forming unit 17 is provided.

The configuration shown in FIG. 11 may be employed in a case where only one expression unit need be connected to the mechanism unit 10.

Figure 12:
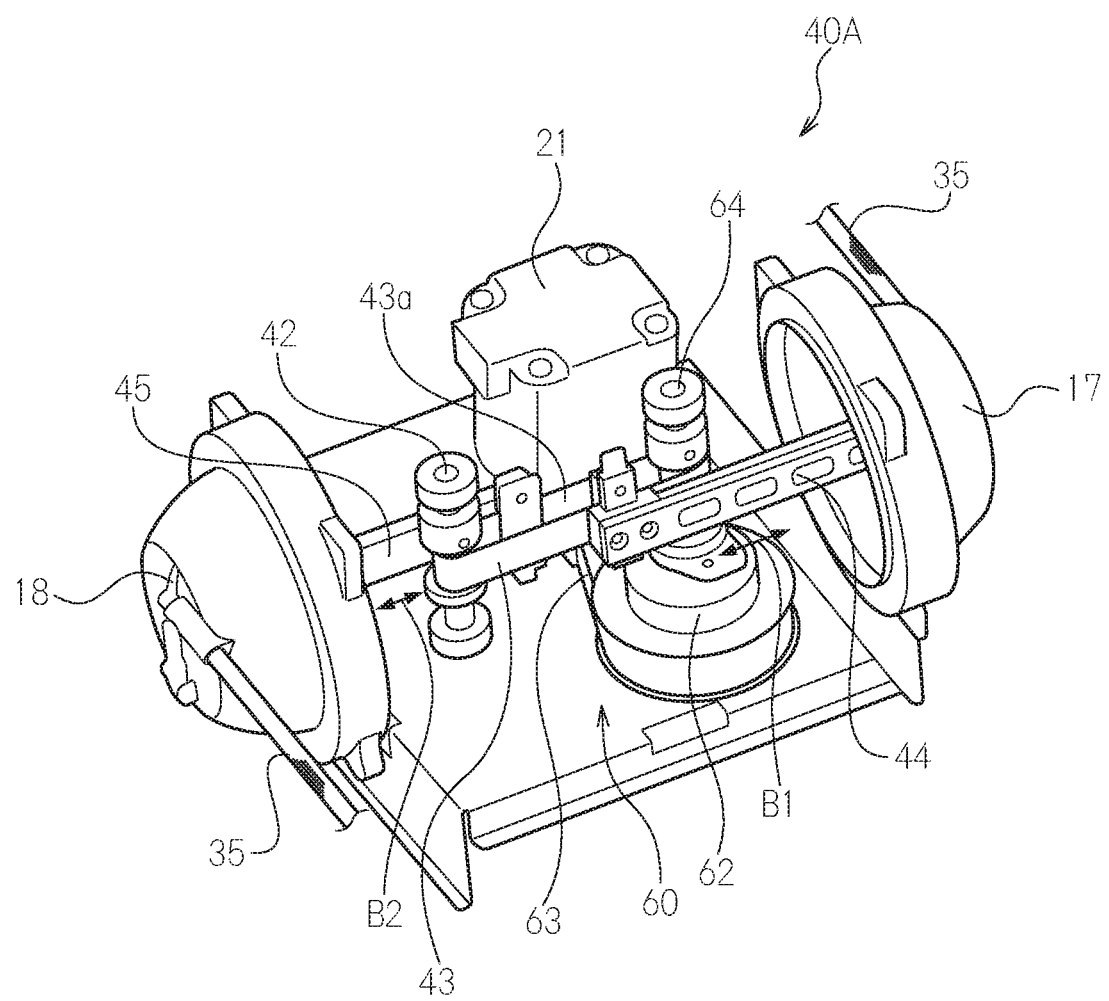
FIG. 12 is a schematic perspective view showing a mechanical configuration of a first modified example of the power driving unit.
Figure 13:
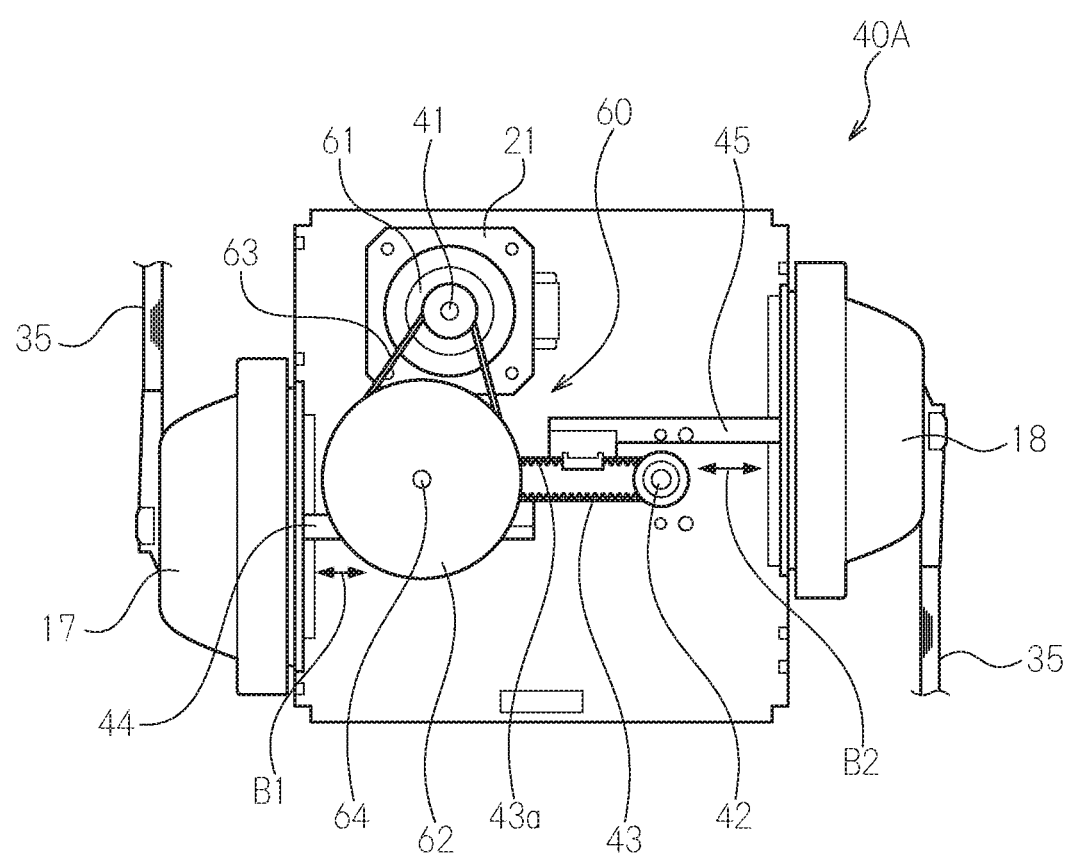
FIG. 13 is a schematic plan view of FIG. 12.

FIG. 12 is a perspective view showing a first modified example of the power driving unit. FIG. 13 is a schematic plan view of FIG. 12.

Note that in this modified example, a case in which the negative pressure forming units 17, 18 described above in relation to FIG. 8 are provided as negative pressure forming units will be described. However, the negative pressure forming units 17A, 18A described in relation to FIG. 10 may also be used as the negative pressure forming units. This applies likewise to a second modified example of the power driving unit, to be described below using FIGS. 14 and 15, a third modified example of the power driving unit, to be described below using FIG. 16, and a fourth modified example of the power driving unit, to be described below using FIG. 17.

A power driving unit 40A according to this modified example differs from the power driving unit 40 described in relation to FIGS. 7 to 9 in further including a reduction gear 60. In this respect, the power driving unit 40A according to this modified example differs from the power driving unit 40 described in relation to FIGS. 7 to 9. The reduction gear 60 reduces the rotation speed of the motor shaft 41.

More specifically, the reduction gear 60 according to this modified example includes a first pulley 61, a second pulley 62, and a belt 63. The first pulley 61 is fixed to the motor shaft 41. The second pulley 62 is provided in a position removed from the first pulley 61, and has a larger diameter than a diameter of the first pulley 61. The belt 63 is an annular endless belt that couples the first pulley 61 and the second pulley 62 to each other. Similarly to the endless belt 43, the belt 63 is preferably formed from a flexible but durable material. For example, a synthetic resin belt capable of slight expansion and contraction, a thin metal plate formed in a belt shape, or the like may be used as the belt 63. All other structures are similar to those of the power driving unit 40 described in relation to FIGS. 7 to 9.

When the motor shaft 41 rotates, a shaft (a shaft of the reduction gear 60) 64 of the second pulley 62, which is coupled to the first pulley 61 by the belt 63, rotates. At this time, since the diameter of the second pulley 62 is larger than the diameter of the first pulley, the rotation speed of the second pulley 62 is lower than the rotation speed of the first pulley 61. In other words, the reduction gear 60 reduces the rotation speed of the motor shaft 41 so as to increase the torque of the motor 21, whereupon the increased torque is transmitted to the shaft 64 of the second pulley 62. The rods 44, 45 then respectively reciprocate horizontally along the arrows B1, B2.

According to this modified example, the power driving unit 40A includes the reduction gear 60, and therefore the power required for the expression operation can be obtained from a smaller output of the motor 21. In other words, the reduction gear 60 is capable of improving the torque of the motor 21. Accordingly, the motor 21 can be reduced in size and weight. As a result, the power driving unit 40A can be constructed extremely compactly.

Further, the reduction gear 60 includes the first pulley 61, the second pulley 62, and the belt 63, and therefore, even when a distance between the motor 21 and the negative pressure forming units 17, 18 is comparatively large, the reduction gear 60 can reduce the rotation speed of the motor shaft 41 reliably by means of a simple structure.

Figure 14:
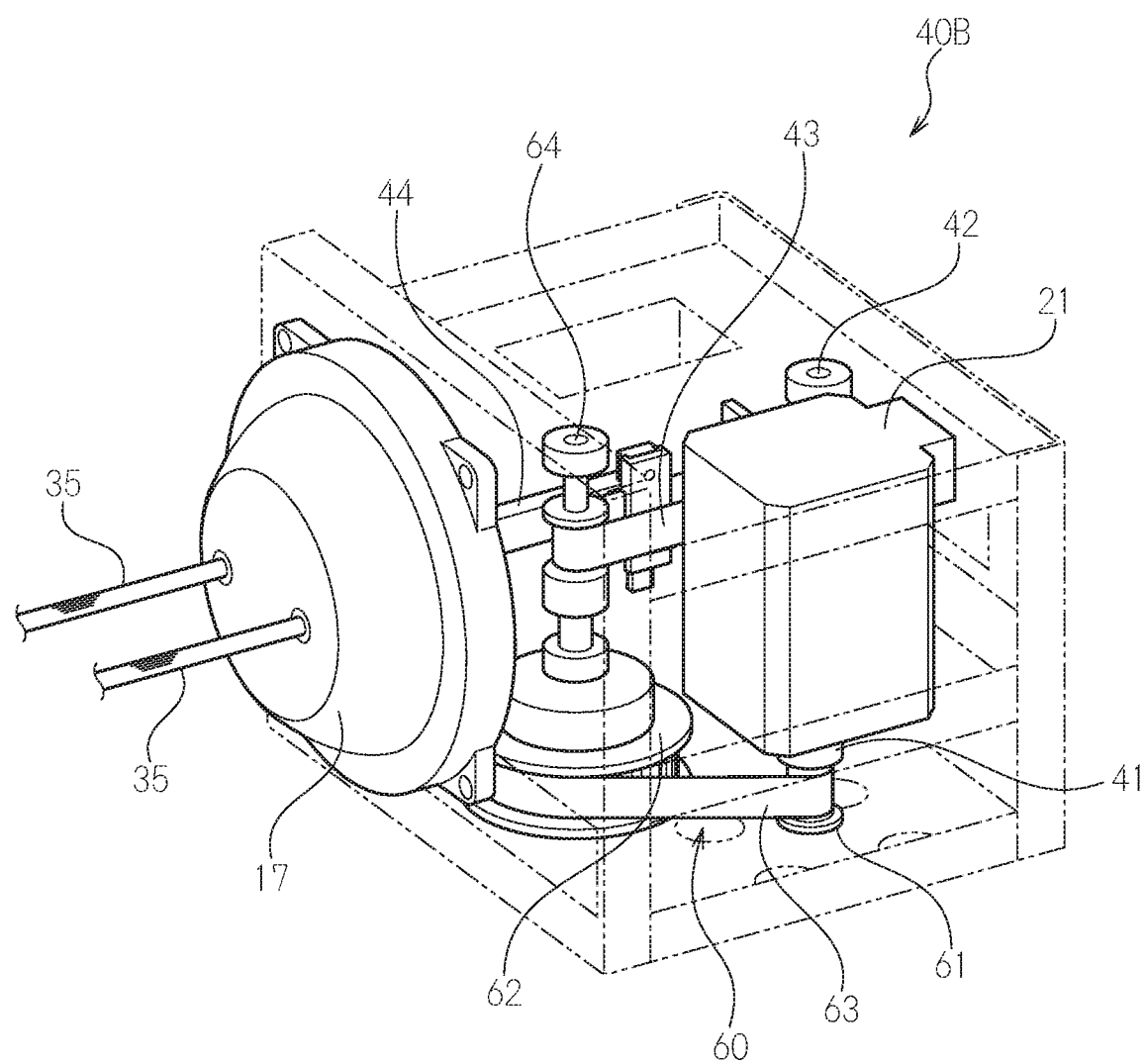
FIG. 14 is a schematic perspective view showing a mechanical configuration of a second modified example of the power driving unit.
Figure 15:
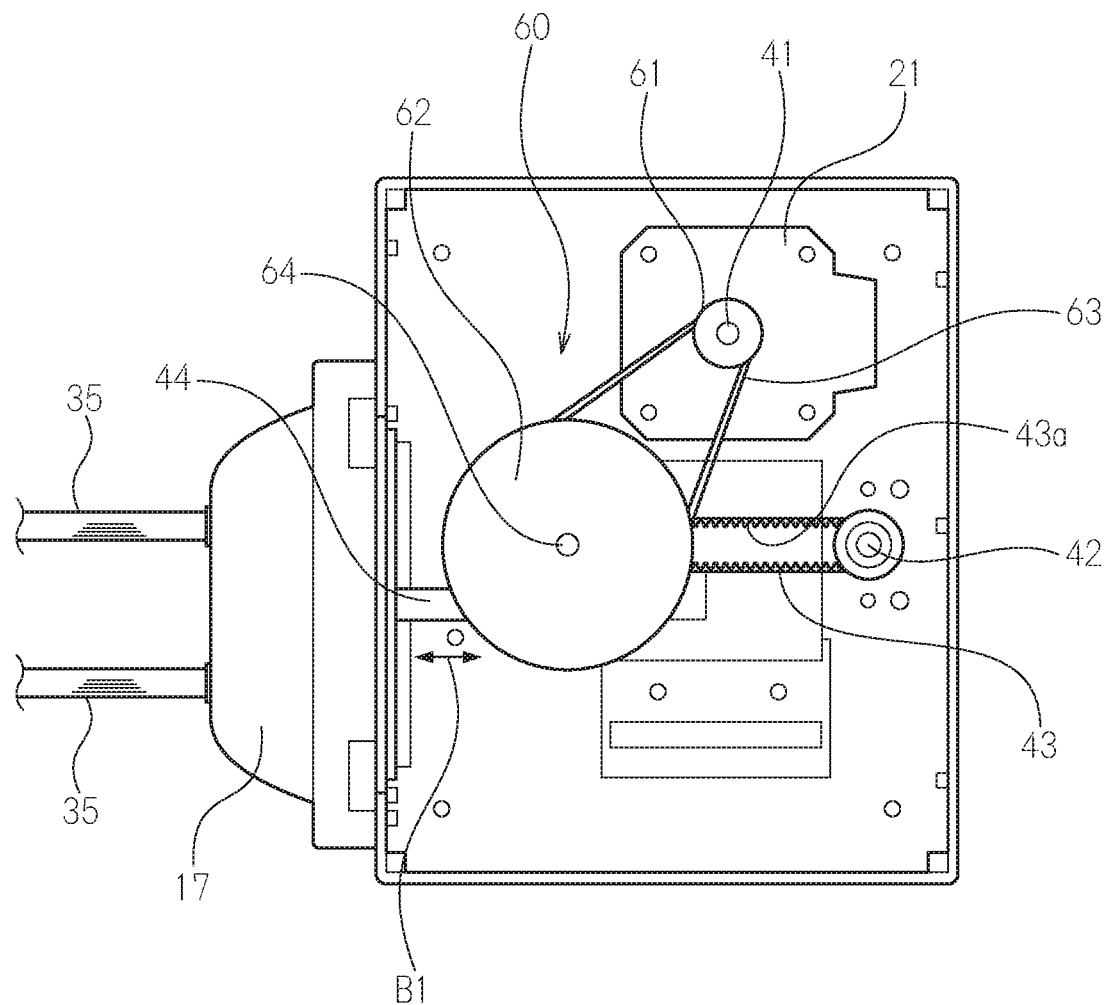
FIG. 15 is a schematic plan view of FIG. 14.

FIG. 14 is a perspective view showing a first modified example of the power driving unit, and FIG. 15 is a schematic plan view of FIG. 14.

In a power driving unit 40B according to this modified example, only one rod 44 is fixed to the endless belt 43. The power driving unit 40B includes the single negative pressure forming unit 17. The two tubes 35 are connected to the negative pressure forming unit 17. Since the reduction gear 60 improves the torque of the motor 21, two expression units 30 may be connected to the single negative pressure forming unit 17 via the two tubes 35. Note that in a case where only one expression unit 30 need be connected to the mechanism unit 10, an opening area of the tube 35 to which the expression unit 30 is not connected is preferably reduced. Means for reducing the opening area of the tube 35 include means for disposing a member that blocks at least a part of the opening of the tube 35 in the opening of the tube 35, for example. Note that the means for reducing the opening area of the tube 35 is not limited to this example. According to this modified example, the power driving unit 40B can be further reduced in size and weight. Moreover, a more favorable negative pressure state is formed, and as a result, a more favorable breast milk suction pressure is maintained.

Figure 16:
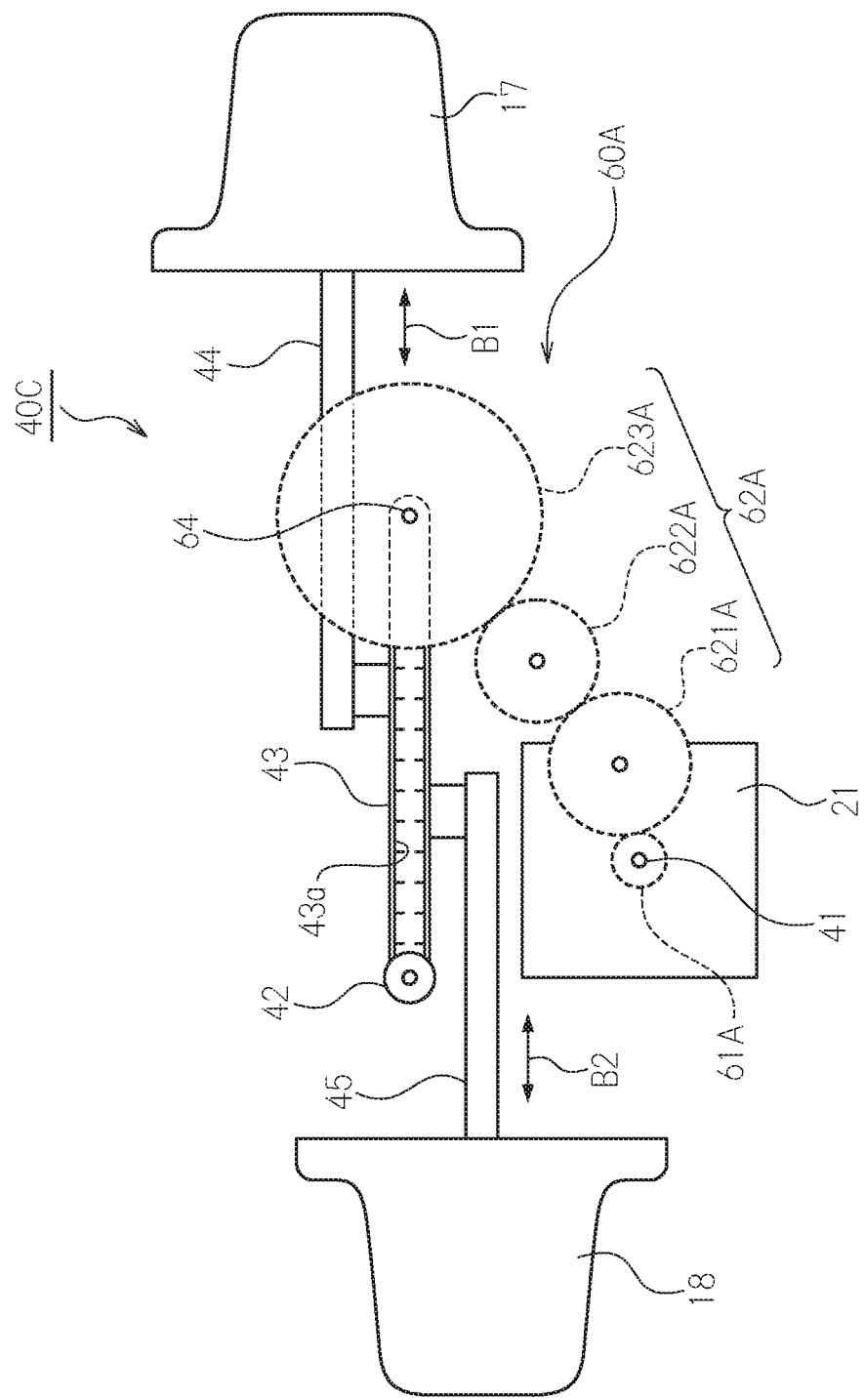
FIG. 16 is a schematic plan view showing a mechanical configuration of a third modified example of the power driving unit.

FIG. 16 is a plan view showing a third modified example of the power driving unit.

A power driving unit 40C according to this modified example differs from the power driving unit 40 described in relation to FIGS. 7 to 9 in further including a reduction gear 60A. In this respect, the power driving unit 40C according to this modified example differs from the power driving unit 40 described in relation to FIGS. 7 to 9. The reduction gear 60A reduces the rotation speed of the motor shaft 41.

More specifically, the reduction gear 60A according to this modified example includes a first gear 61A and a gear train 62A having at least one gear. The first gear 61A is fixed to the motor shaft 41. The gear train 62A includes a second gear 621A, a third gear 622A, and a fourth gear 623A, and meshes with the first gear 61A so as to reduce the rotation speed of the first gear 61A. Note that there are no particular limitations on the number of gears forming the gear train 62A, and one, two, or more gears may be used. All other structures are similar to those of the power driving unit 40 described in relation to FIGS. 7 to 9.

When the motor shaft 41 rotates, a shaft (the shaft of the reduction gear 60A) 64 of the fourth gear 623A, which serves as the final stage of the gear train 62A meshing with the first gear 61A, rotates. At this time, the gear train 62A reduces the rotation speed of the first gear 61A. In other words, the reduction gear 60A reduces the rotation speed of the motor shaft 41 so as to increase the torque of the motor 21, whereupon the increased torque is transmitted to the shaft 64 of the fourth gear 623A serving as the final stage of the gear train 62A. The rods 44, 45 then respectively reciprocate horizontally along the arrows B1, B2.

According to this modified example, the power driving unit 40C includes the reduction gear 60A, and therefore, as described above in relation to FIGS. 12 and 13, the power driving unit 40C can be constructed extremely compactly. Moreover, the torque of the motor 21 is transmitted by a plurality of gears, and therefore the reduction gear 60A can be prevented from slipping when transmitting the output of the motor 21 to the rods 44, 45. Furthermore, a larger output from the motor 21 can be transmitted to the rods 44, 45.

Figure 17:
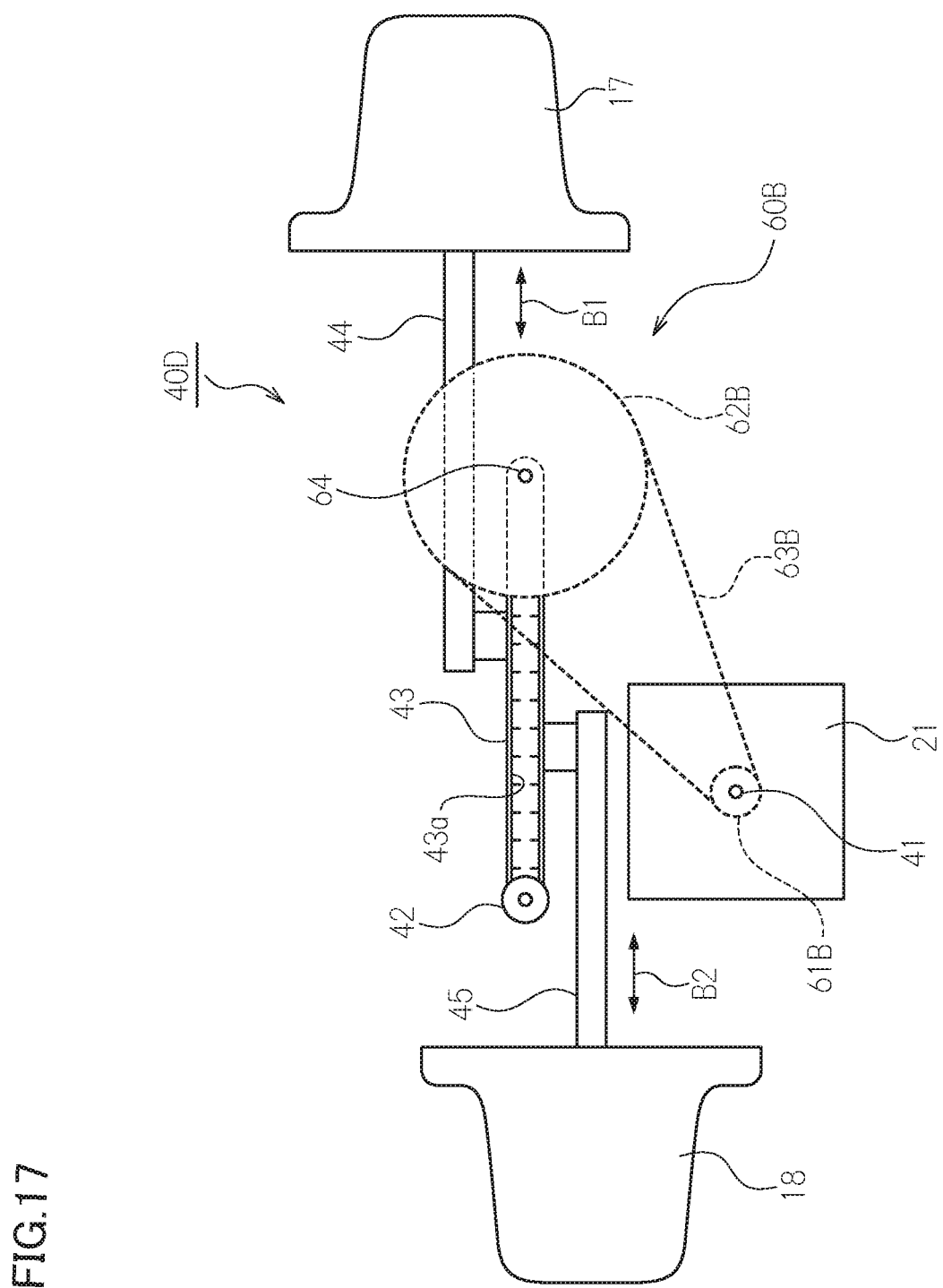
FIG. 17 is a schematic plan view showing a mechanical configuration of a fourth modified example of the power driving unit.

FIG. 17 is a plan view showing a fourth modified example of the power driving unit.

A power driving unit 40D according to this modified example differs from the power driving unit 40 described in relation to FIGS. 7 to 9 in further including a reduction gear 60B. In this respect, the power driving unit 40D according to this modified example differs from the power driving unit 40 described in relation to FIGS. 7 to 9. The reduction gear 60B reduces the rotation speed of the motor shaft 41.

More specifically, the reduction gear 60B according to this modified example includes a first sprocket 61B, a second sprocket 62B, and a chain 63B. The first sprocket 61B is fixed to the motor shaft 41. The second sprocket 62B is provided in a position removed from the first sprocket 61B, and has a larger number of teeth than a number of teeth of the first sprocket 61B. The chain 63B is an annular endless chain that couples the first sprocket 61B and the second sprocket 62B to each other. All other structures are similar to those of the power driving unit 40 described in relation to FIGS. 7 to 9.

When the motor shaft 41 rotates, a shaft (the shaft of the reduction gear 60) 64 of the second sprocket 62B, which is coupled to the first sprocket 61B by the chain 63B, rotates. At this time, since the number of teeth of the second sprocket 62B is larger than the number of teeth of the first sprocket 61B, the rotation speed of the second sprocket 62B is lower than the rotation speed of the first sprocket 61B. In other words, the reduction gear 60B reduces the rotation speed of the motor shaft 41 so as to increase the torque of the motor 21, whereupon the increased torque is transmitted to the shaft 64 of the second sprocket 62B. The rods 44, 45 then respectively reciprocate horizontally along the arrows B1, B2.

According to this modified example, the power driving unit 40D includes the reduction gear 60B, and therefore, as described above in relation to FIGS. 12 and 13, the power driving unit 40D can be constructed extremely compactly. Moreover, the reduction gear 60B includes the first sprocket 61B, the second sprocket 62B, and the chain 63B, and therefore, even when the distance between the motor 21 and the negative pressure forming units 17, 18 is comparatively large, the reduction gear 60B can be prevented from slipping when transmitting the output of the motor 21 to the rods 44, 45. Furthermore, a larger output from the motor 21 can be transmitted to the rods 44, 45.

Figure 18:
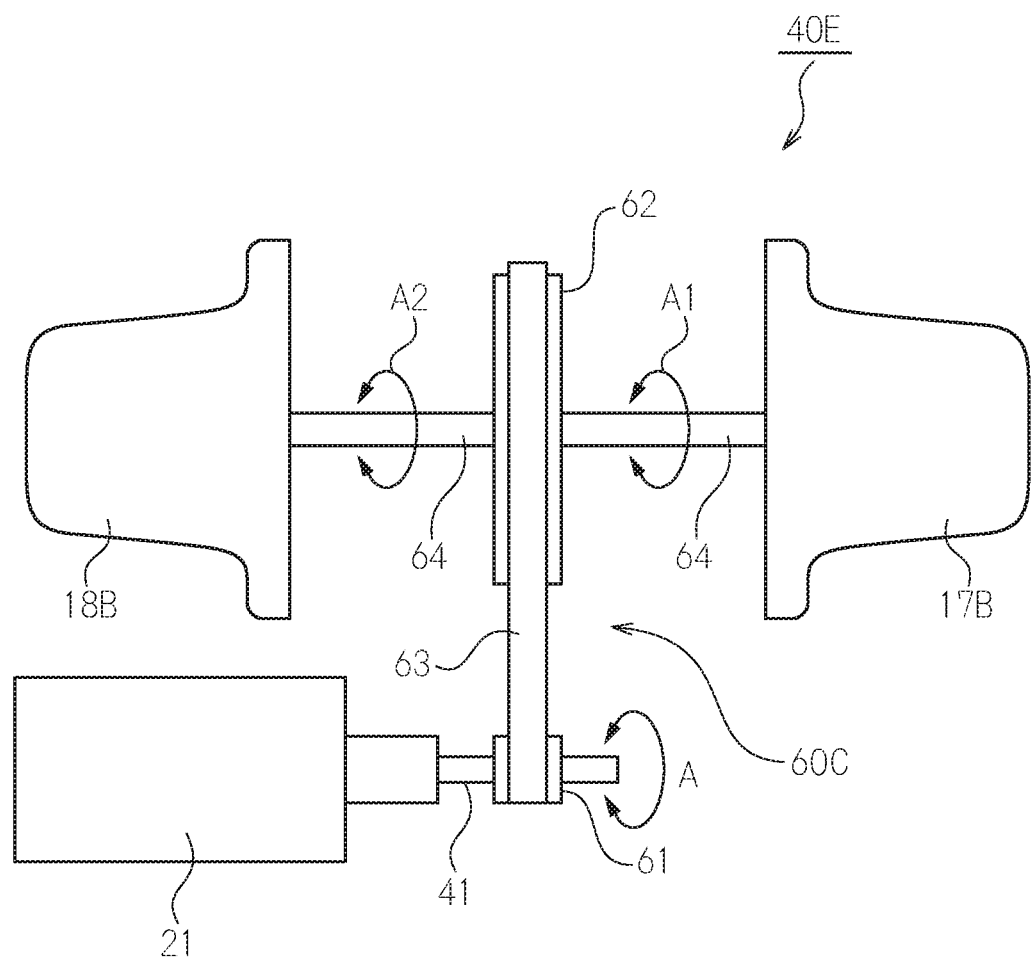
FIG. 18 is a schematic plan view showing a mechanical configuration of a fifth modified example of the power driving unit.
Figure 19:
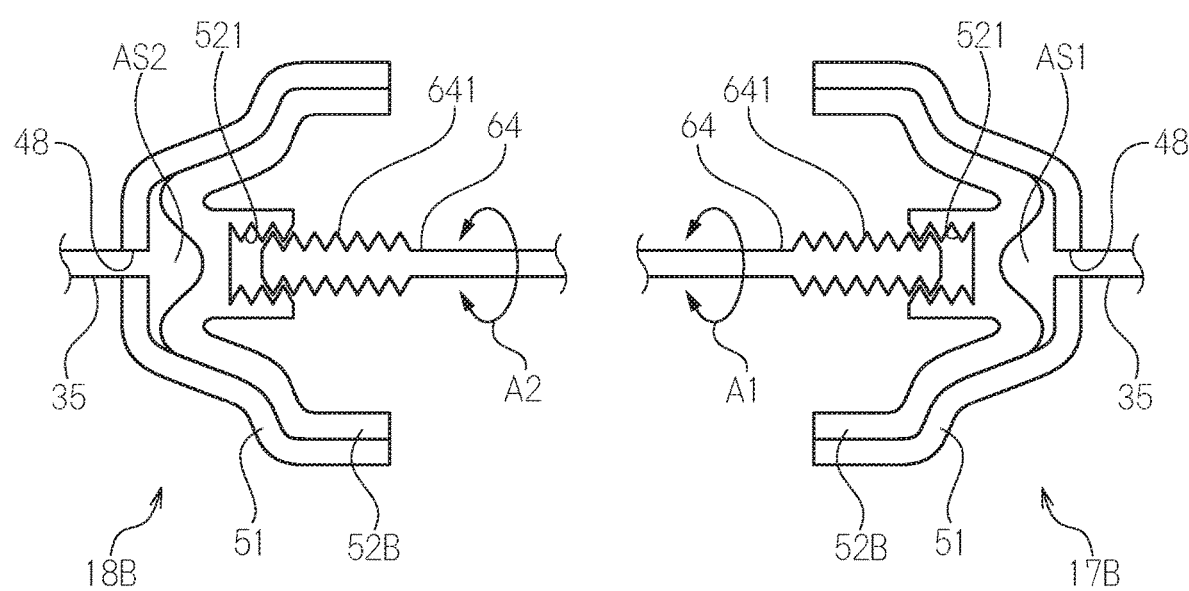
FIG. 19 is an illustrative view showing an example of main parts of a second modified example of the negative pressure forming unit.

FIG. 18 is a plan view showing a fifth modified example of the power driving unit. FIG. 19 shows a second modified example of the negative pressure forming unit.

A power driving unit 40E according to this modified example differs from the power driving unit 40 described in relation to FIGS. 7 to 9 in further including a reduction gear 60C. In this respect, the power driving unit 40E according to this modified example differs from the power driving unit 40 described in relation to FIGS. 7 to 9. The reduction gear 60C reduces the rotation speed of the motor shaft 41.

More specifically, the reduction gear 60C, similarly to the reduction gear 60 described above in relation to FIG. 12, includes the first pulley 61, the second pulley 62, and the belt 63. The motor shaft 41 and the shaft 64 of the second pulley 62 extend in a reciprocation direction (a displacement direction) of deforming members 52B of negative pressure forming units 17B, 18B. Accordingly, as indicated by arrows A1, A2 in FIG. 18, the shaft 64 of the second pulley 62 rotates about an axis extending in the reciprocation direction of the deforming members 52B. In this respect, the reduction gear 60C differs from the reduction gear 60 described above in relation to FIG. 12.

The negative pressure forming units 17B, 18B according to this modified example include the outside members 51 and the deforming members (elastic bodies) 52B. The deforming members 52B are durable film-form members such as membranes or diaphragms that are easily elastically deformed and do not break even when deformed repeatedly, and include female screws 521 provided in inside ends thereof.

Male screws 641 are provided on respective ends of the shaft 64 of the second pulley 62 so as to be fitted into the female screws 521 of the deforming members 52B. All other structures are similar to those of the power driving unit 40 described in relation to FIGS. 7 to 9 and the negative pressure forming units 17, 18 described in relation to FIG. 8.

When the motor shaft 41 rotates, the shaft (the shaft of the reduction gear 60) 64 of the second pulley 62, which is coupled to the first pulley 61 by the belt 63, rotates. At this time, since the diameter of the second pulley 62 is larger than the diameter of the first pulley, the rotation speed of the second pulley 62 is lower than the rotation speed of the first pulley 61. In other words, the reduction gear 60 reduces the rotation speed of the motor shaft 41 so as to increase the torque of the motor 21, whereupon the increased torque is transmitted to the shaft 64 of the second pulley 62.

When the shaft 64 of the second pulley 62 rotates, the deforming members 52B, which have the female screws 521 fitted onto the male screws 641 of the shaft 64 of the second pulley 62, are pulled inward. At this time, the male screw 641 and the female screw 521 forming a pair on one of the two sides preferably serve as a right screw, and the male screw 641 and the female screw 521 forming a pair on the other side preferably serve as a left screw. In this case, when the shaft 64 of the second pulley 62 rotates in one direction, the deforming members 52B are both pulled inward. As a result, negative pressure forming spaces (regions in which negative pressure is generated) indicated by reference symbols AS1 and AS2 are created in the negative pressure forming units 17B, 18B.

According to this modified example, the rods 44, 45 described above in relation to FIG. 12 are not required. As a result, the power driving unit 40E can be constructed even more compactly. Further, similar effects to the effects described in relation to FIG. 12 are obtained.

Figure 20:
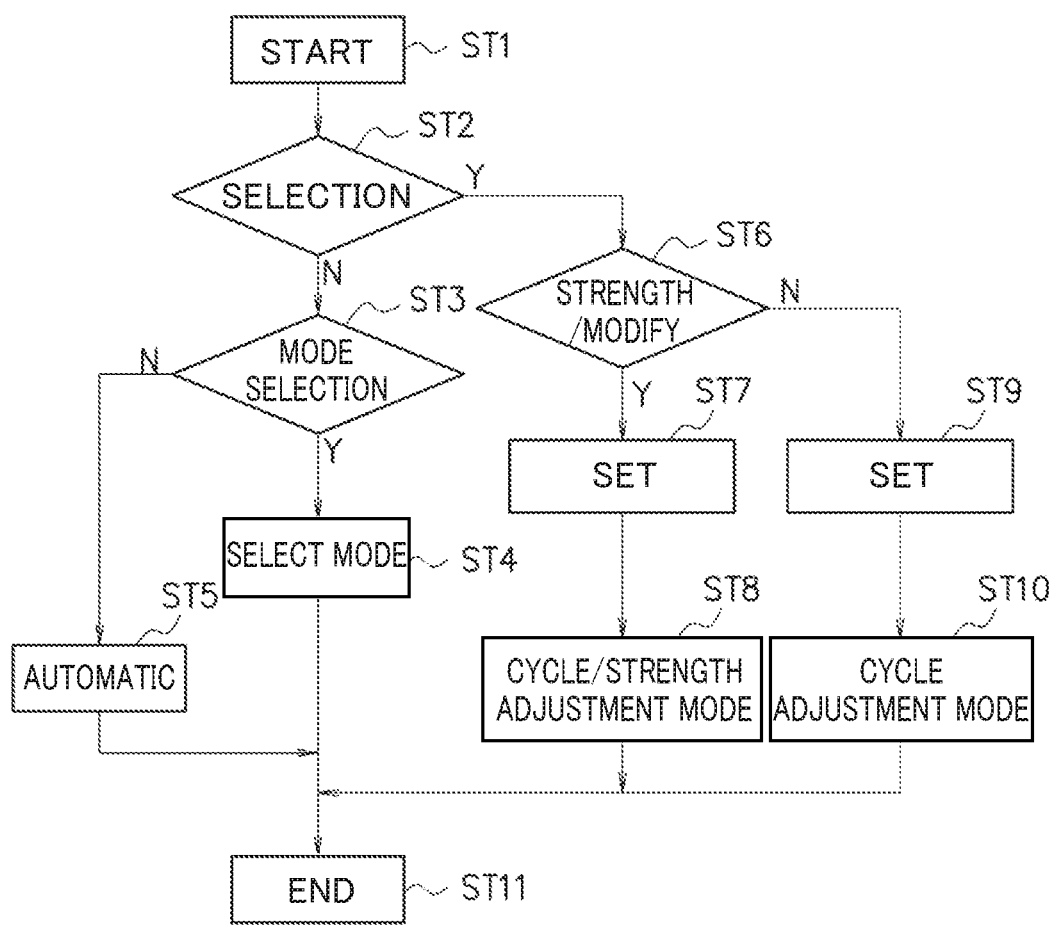
FIG. 20 is a flowchart illustrating an example of an operation of the breast pump according to this embodiment of the present invention.

Next, an example operation of the breast pump according to this embodiment will be described with reference to FIG. 20.

The housing 10 shown in FIG. 1 and the horn-shaped expressing unit 36 of the expression unit 30 are brought into contact with the breast (not shown) of the user.

Next, the breast pump is started by selecting/operating the start switch from the operating buttons 15b while viewing the display unit 15a on the operating panel 15 of the mechanism unit 10 shown in FIG. 1 (ST1). In other words, a start instruction is issued, in response to which the control board 25 issues an instruction to the switching power supply 24, whereupon a signal is transmitted from the switching power supply 24 to the motor driver board 22 in order to start the motor 21.

Next, the operating buttons 15b are operated in accordance with guidance and the like on the display unit 15a in order to select an operating mode (ST2). When, during selection of the operating mode, an operating mode prepared in advance, as will be described below, is to be selected or an automatic operation performed in a single set operating mode is to be selected, the operation advances to mode selection in step 3.

In step 3, a determination is made either to execute expression by selecting one of a plurality of prepared operating modes or to select an automatic operation mode prepared as a single default operating pattern, whereupon an instruction is issued by the operating buttons 15b.

When the automatic operation mode is selected, relevant data stored in the memory of the control board 25 are read and transmitted to the motor driver board 22, whereupon the operation advances to step 5. In step 5, a predetermined expression operation is executed, whereupon the operation is terminated (ST5, ST11).

When, on the other hand, the magnitude of the negative pressure to be applied during expressing, the expressing frequency, and so on are to be selected and set individually in step 2 in accordance with the preferences and so on of the user, the operation advances to step 6. In other words, when settings including "suction pressure (magnitude of negative pressure during expressing)" are to be set, the settings are selected by operating the operating buttons 15b such that the control board 25 issues an instruction to the motor driver board 22 (ST7).

Figure 21:
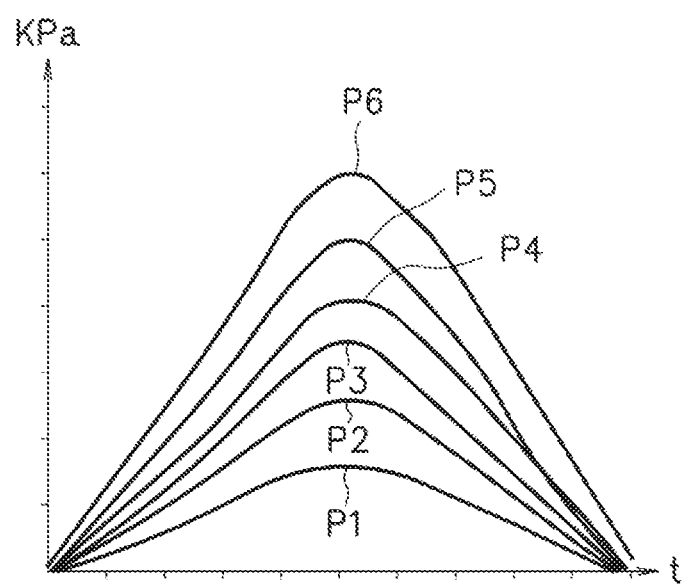
FIG. 21 is a waveform graph illustrating operating states of the breast pump according to this embodiment of the present invention.

FIG. 21 is a graph illustrating operating states of the breast pump according to this embodiment.

In the figure, the suction pressure is shown as an amplitude on the graph, and represented by numerical values on the vertical axis. More specifically, a waveform P2 indicates a larger "suction pressure" than a waveform P1, whereupon the suction pressure gradually increases from P3 to P6. The suction pressure is commensurate with the rotation angle of the rotation shaft of the motor, illustrated in FIG. 6, and the volume of the negative pressure forming spaces AS1 and AS2 shown in FIG. 8.

In other words, the suction pressure can be controlled in accordance with the number of drive pulses generated by the motor driver board 22 in FIG. 5.

Further, in FIG. 21, the horizontal axis of the graph shows time t, and the size of the horizontal axis of the waveform indicates the time required for the arrow A in FIG. 6 to reciprocate. As the rotation speed increases, the numerical value of the horizontal axis t of the waveform decreases, leading to an increase in frequency. In other words, the expression cycle shortens. Hence, the expression frequency can be controlled by adjusting the pulse width of the drive pulse.

When step 7 is selected, the operation advances to step 8, where both the number of drive pulses and the pulse width of the drive pulse are modified (ST8). Note that in a case where step 8 is executed, user-friendliness can be improved by preparing a plurality of combinations of predetermined numbers of drive pulses and pulse widths in the form of table data and attaching titles that the user can easily understand thereto so that the user can select one of the plurality of variations as desired. Hence, in step 8, after modifying the number of drive pulses and the pulse width thereof, a predetermined expression operation is performed, whereupon the operation is terminated (ST11).

Furthermore, when a negative result is obtained in step 6, this means that the suction pressure does not have to be modified, and therefore the operation advances to step 9, where the operating buttons 15b are operated such that the control board 25 advances to step 10. In step 10, the "expression cycle", or in other words the pulse width of the drive pulse, is modified, whereupon a predetermined expression operation is then performed. The operation is then terminated (ST11).

With the breast pump according to this embodiment, as described above, the suction pressure and the cycle (the speed at which the negative pressure is increased and reduced) of the breast pump can be controlled individually as soon as the breast pump is started, and therefore the user can specify these two elements individually, leading to an improvement in convenience.

More specifically, the expression cycle and the suction pressure can both be reduced, the cycle can be increased while reducing the suction pressure, and vice versa. Hence, the user can set the expression cycle and the suction pressure as desired in accordance with her preferences extremely quickly after starting to use the breast pump, which is extremely convenient.

Moreover, a desired suction pressure can be obtained immediately after the start of an operation, thereby entirely eliminating the need for an ancillary structure having a comparatively large volume, such as a conventional "buffer" used to form negative pressure, and as a result, the breast pump can be formed more compactly.

Incidentally, the present invention is not limited to the embodiment described above.

For example, in the mechanism unit of FIG. 7 or 8, the rod 44 may be omitted, and the movements B1, B2 may be realized by mounting teeth on the motor shaft 41 and meshing a rack with the teeth.

The example operation may also be modified. For example, a preparatory operation mode using a predetermined drive pulse may be provided in advance of the expressing modes of the flowchart shown in FIG. 20, and the user may set the suction pressure and/or the expression cycle during the preparatory operation.

As regards default values of the operation executed in step 5, a plurality of default values may be selected in accordance with each user, for example the age, physique, and so on of the user. Further, the default values may be replaced with data obtained from an operation history following the most recent modification of the settings.

Note that the individual configurations of the embodiments and modified examples described above may be omitted or combined with other configurations not described above as required.

REFERENCE SIGNS LIST

10 Mechanism unit
15 Display unit
17, 17A, 17B, 18, 18A, 18B Negative pressure forming unit
21 (Stepping) motor
41 Motor shaft
42 Support shaft
43 Endless belt
44, 45 Rod
30 Expression unit

The invention claimed is:

1. A breast pump comprising: a variable pressure generating unit connected to an expressing unit that is brought into contact with a breast of a user, and alternately forming a negative pressure state below atmospheric pressure and a higher pressure than the pressure of the negative pressure state,
the variable pressure generating unit including:
a power driving unit including a stepping motor that is capable of repeating a rotation either in a normal direction or in a reverse direction with a cycle period,
an endless belt that is attached to the stepping motor such that the endless belt makes a rotation in accordance with the rotation of the stepping motor, and
a pair of linear moving bodies that are in a linear shape each having a distal end wherein the liner moving bodies are attached to the endless belt at different positions, which are separated, such that two of the distal ends move in opposite directions in accordance with the rotation of the endless belt; and
a pair of negative pressure forming units each of which corresponds to one of the linear moving bodies, has an inner space thereinside wherein the inner space is surrounded partially or entirely with an elastic body, and each of the negative pressure forming units is configured to create the negative pressure state by causing the elastic body to deform, wherein
the negative pressure forming unit is coupled to the expressing unit, and
the stepping motor has a motor shaft to rotate and is configured to modify an amplitude of the cycle period and a time length of the cycle period during negative pressure formation as desired,
each of the distal ends of the linear moving bodies is connected to the elastic body of the corresponding negative pressure forming unit, and reciprocates linearly along a rotation direction of the motor shaft such that, when the stepping motor repeat to rotate the endless belt in the normal direction and in the reverse direction with the cycle period, the distal ends repeat to deform the elastic bodies, increasing and reducing a size of the inner space in accordance with the cycle period, such that the negative pressure forming units generates negative pressure in the corresponding negative pressure forming unit as the motor shaft repeatedly rotates in the normal direction and in the reverse direction.

2. The breast pump according to claim 1, further comprising:
a mechanism unit installed with the power driving unit, wherein
the expression unit is connected to the mechanism unit,
the negative pressure formed by the mechanism unit is transmitted to the expression unit.

3. The breast pump according to claim 1, wherein
the power driving unit further includes
a support shaft provided in parallel with the motor shaft
the endless belt is disposed between the motor shaft and the support shaft, and
the power driving unit forms the negative pressure by transmitting a reciprocation operation of the endless belt to the negative pressure forming unit.

4. The breast pump according to claim 1, wherein the power driving unit further includes:
a reduction gear for reducing a rotation speed of the motor shaft; and
a support shaft provided in parallel with a shaft of the reduction gear,
the endless belt is disposed between the shaft of the reduction gear and the support shaft, and
the power driving unit forms the negative pressure by transmitting a reciprocation operation of the endless belt to the negative pressure forming unit.

5. The breast pump according to claim 4, wherein the reduction gear includes:

a first pulley fixed to the motor shaft;
a second pulley having a larger diameter than a diameter of the first pulley; and
a belt that couples the first pulley and the second pulley to each other, and
wherein a shaft of the second pulley serves as the shaft of the reduction gear.

6. The breast pump according to claim 4, wherein the reduction gear includes:
a first gear fixed to the motor shaft; and
a gear train that meshes with the first gear in order to reduce a rotation speed of the first gear, and includes at least one gear, and
wherein a shaft of a final stage gear of the gear train serves as the shaft of the reduction gear.

7. The breast pump according to claim 4, wherein the reduction gear includes:
a first sprocket fixed to the motor shaft;
a second sprocket having a larger number of teeth than a number of teeth of the first sprocket; and
a chain that couples the first sprocket and the second sprocket to each other, and
wherein a shaft of the second sprocket serves as the shaft of the reduction gear.

8. The breast pump according to claim 1, wherein
one of the elastic bodies is a dome-shaped film-form member to which one end of the linear moving body is fixed, and the size of the inner space of the negative pressure forming unit in which the negative pressure is generated is increased and reduced in accordance with displacement of the elastic body in a direction of a linear movement of the linear moving body.

9. The breast pump according to claim 1, wherein
one of the elastic bodies is a film-form member having a bellows structure capable of expansion and contraction, and the size of the inner space of the negative pressure forming unit in which the negative pressure is generated is increased and reduced in accordance with expansion and contraction of the one of the elastic bodies in a direction of a linear movement of the linear moving body.

10. The breast pump according to claim 1, wherein
each of the elastic bodies is a dome-shaped film-form member to which one end of the linear moving body is fixed, and the size of the inner space of the negative pressure forming unit in which the negative pressure is generated is increased and reduced in accordance with displacement of the elastic body in a direction of a linear movement of the linear moving body.

11. The breast pump according to claim 1, wherein
each of the elastic bodies is a film-form member having a bellows structure capable of expansion and contraction, and the size of the inner space of the negative pressure forming unit in which negative pressure is generated is increased and reduced in accordance with expansion and contraction of the elastic body in a direction of a linear movement of the linear moving body.

* * * * *